United States Patent [19]

Rossing

[11] Patent Number: 5,403,352
[45] Date of Patent: Apr. 4, 1995

[54] METHOD AND APPARATUS FOR DETECTION AND TREATMENT OF TACHYCARDIA AND FIBRILLATION

[75] Inventor: Martin A. Rossing, Ramsey, Minn.
[73] Assignee: Medtronic, Inc., Minneapolis, Minn.
[21] Appl. No.: 157,360
[22] Filed: Nov. 23, 1993
[51] Int. Cl.⁶ .......................... A61N 1/37; A61N 1/39
[52] U.S. Cl. ........................................ 607/4; 607/14; 128/705
[58] Field of Search ............................ 607/5, 4, 9, 14; 128/702, 705; 364/413.06

[56] References Cited

U.S. PATENT DOCUMENTS

| | | |
|---|---|---|
| 4,375,817 | 3/1983 | Engle . |
| 4,384,585 | 5/1983 | Zipes . |
| 4,548,209 | 10/1985 | Wielders . |
| 4,577,633 | 3/1986 | Berkovits . |
| 4,587,970 | 5/1986 | Holley . |
| 4,693,253 | 9/1987 | Adams . |
| 4,726,380 | 2/1988 | Vollmann . |
| 4,800,883 | 1/1989 | Winstrom . |
| 4,819,643 | 4/1989 | Menken . |
| 4,830,006 | 5/1989 | Haluska . |
| 4,880,004 | 11/1989 | Baker, Jr. . |
| 4,880,005 | 11/1989 | Pless . |
| 4,949,719 | 8/1990 | Pless . |
| 4,953,551 | 9/1990 | Mehra . |
| 4,971,058 | 11/1990 | Pless . |

OTHER PUBLICATIONS

"Onset and Stability for Ventricular Tachyarrhythmia Detection in an Implantable Pacer-Cardioverter Defibrillator", by Olson et al., in Computers in Cardiology, Oct. 7-10, 1986, pp. 167-170.

"Reliable R-Wave Detection from Ambulatory Subjects", by Thakor, published in Biomed Sci Instrum, 14:67-72. 1978.

Primary Examiner—William E. Kamm
Assistant Examiner—Kennedy J. Schaetzle
Attorney, Agent, or Firm—Reed A. Duthler; Harold R. Patton

[57] ABSTRACT

An automatic implantable device for detecting and differentiating between tachyarrhythmias in order to therapeutically stimulate the heart in response thereto, particularly for distinguishing fibrillation from tachycardia and to provide appropriate therapies for each condition. The event intervals between successive heart depolarizations are measured, stored and classified as within fibrillation or tachycardia interval ranges. The numbers of intervals falling within the fibrillation and tachycardia interval ranges are employed to distinguish fibrillation from tachycardia. The number of intervals required to detect and discriminate between tachycardia and fibrillation in situations where the tachyarrhythmia includes intervals in both interval ranges is reduced by adjusting the interval ranges as a function of the relative distribution of measured intervals within the interval ranges.

10 Claims, 4 Drawing Sheets

METHOD AND APPARATUS FOR DETECTION AND TREATMENT OF TACHYCARDIA AND FIBRILLATION

BACKGROUND OF THE INVENTION

This invention relates to devices which detect and/or treat tachyarrhythmias (rapid heart rhythms), and more specifically, to mechanisms to distinguish among various tachyarrhythmias and to provide appropriate therapies to treat the identified tachyarrhythmias.

Early automatic tachyarrhythmia detection systems for automatic cardioverter/defibrillators relied upon the presence or absence of electrical and mechanical heart activity (such as intra-myocardial pressure, blood pressure, impedance, stroke volume or heart movement) and/or the rate of the electrocardiogram to detect hemodynamically compromising ventricular tachycardia or fibrillation.

In pacemaker/cardioverter/defibrillators presently in clinical evaluation, fibrillation is distinguished from ventricular tachycardia using rate based criteria, In such devices, it is common to specify the rate or interval ranges that characterize a tachyarrhythmia as opposed to fibrillation. However, some patients may suffer from ventricular tachycardia and ventricular fibrillation which have similar or overlapping rates, making it difficult to distinguish low rate fibrillation from high rate tachycardia. In addition, ventricular fibrillation may display R—R intervals which may vary considerably, resulting in intervals that may fall within both the tachycardia and fibrillation rate or interval ranges, or outside both.

Presently available pacemaker/cardioverter/defibrillator arrhythmia control devices, such as the Model 7216A and 7217B pacemaker/cardioverter/defibrillator devices available from Medtronic, Inc., employ programmable fibrillation interval ranges and tachycardia detection interval ranges which are adjacent to one another but do not overlap. In these Medtronic devices in particular, the interval range designated as indicative of fibrillation consists of intervals less than a programmable interval (FDI) and the interval range designated as indicative of ventricular tachycardia consists of intervals less than a programmable interval (TDI) and greater than or equal to FDI. R—R intervals are counted to provide a count of R—R intervals falling within the tachycardia interval range (VTEC) and a count of intervals within the fibrillation range (VFEC). VFEC is a count of how many of the preceding series of a predetermined number (FEB) of R—R intervals is less than or equal to FDI. The VTEC count is incremented in response to R—R intervals that are greater than or equal to FDI but shorter than TDI, is reset to zero in response to intervals longer than or equal to TDI and is insensitive to intervals less than FDI. VTEC is compared to a programmed value (VTNID) and VFEC is compared to a corresponding programmable value (VFNID). When one of the counts equals its corresponding programmable value, the device diagnoses the presence of the corresponding arrhythmia, i.e., fibrillation or tachycardia and delivers an appropriate therapy, e.g., anti-tachycardia pacing, a cardioversion pulse or a defibrillation pulse. In addition, the physician may optionally program the device to require that measured R—R intervals meet a rapid onset criterion before the VTEC count can be incremented and may also optionally program the device to require that a rate stability criterion be met with each successive measured R—R interval in order to increment VTEC and that otherwise VTEC will be reset to zero. This detection system has proven effective in distinguishing between fibrillation and ventricular tachycardia so that appropriate therapies may be delivered. However, in rare instances, the detection methodology may require a sequence of a greater number of rapid heart beats than might optimally be desired to determine whether the rapid rhythm is due to fibrillation or tachycardia. Moreover, an improved level of accuracy in classifying rhythms close to FDI in average R—R interval duration is also believed desirable.

SUMMARY OF THE INVENTION

It is an object of the present invention to provide for accurate detection of and discrimination between tachycardia and fibrillation. It is a further object of the present invention to provide for detection of these arrhythmias in as few heartbeats as possible, consistent with accurate detection.

In accordance with the present invention, it is realized that because of the randomness of intervals between depolarizations during fibrillation or because of the characteristics of a patient's heart rhythms, fibrillation and tachycardia may include such intervals of similar duration. Thus, in a device which defines interval or rate ranges as indicative of fibrillation and tachycardia, intervals falling within the range defined as indicative of fibrillation may in fact be occurring during tachycardia, and vice versa. Moreover, either tachycardia or fibrillation may include intervals in both rate or interval ranges, delaying detection and identification of the arrhythmia.

The present invention addresses these problems by increasing or decreasing the duration of the minimum interval indicative of fibrillation and/or the maximum interval indicative of tachycardia (which, in the disclosed embodiment are essentially the same value) as a function of the measured cycle lengths in a sample of the "N" most recent intervals between depolarizations, that fall within the interval ranges indicative of tachycardia or fibrillation. During the detection of a rhythm containing a series of fast such intervals, the invention determines whether the number of intervals within the interval range indicative of fibrillation exceeds a predetermined number or percentage. If so, the value of the minimum interval indicative of fibrillation is incremented. The invention may also or alternatively determine whether the number of such intervals within the interval range indicative of tachycardia exceeds a predetermined number or percentage. If so, the value of the minimum interval indicative of fibrillation is decremented. Thus, the detection criteria are biased toward detection of fibrillation or tachycardia depending on the relative numbers of measured intervals falling within the associated rate zones. This bias increases the speed of detection by making it more likely that detected intervals will assist in meeting the detection criteria for one of these arrhythmias than the other. In rhythms with average intervals between depolarizations near the minimum interval duration which defines the dividing line between the tachycardia and fibrillation interval ranges, the invention in general reduces the total number of intervals required to satisfy the detection criteria for fibrillation or tachycardia.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which.

DETAILED DESCRIPTION OF THE PREFERRED EMBODIMENT

In the embodiment of the invention discussed below, the tachycardia and fibrillation detection criteria discussed above in conjunction with the Medtronic Model 7216 and Model 7217 implantable pacemaker/cardioverter/defibrillators are employed, and the following discussion of the present invention should be understood in this context, with the present invention being employed in this embodiment to adjust the dividing point FDI between the interval ranges associated with ventricular tachycardia and ventricular fibrillation. However, while the specific embodiment disclosed below is directed to distinguishing between ventricular tachycardia and fibrillation, it is also believed that the invention may also be usefully be practiced in the context of a device for treating atrial tachyarrhythmias. Moreover, the value of the present invention is not limited to the context of the specific detection criteria disclosed, but is believed workable and valuable in the context of any devices which distinguish between tachycardia and fibrillation using rate or interval based criteria.

Figure 1:
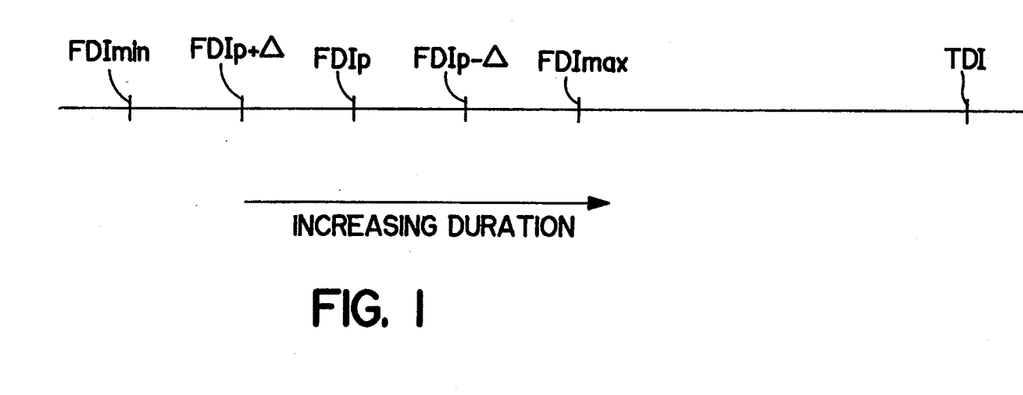
FIG. 1 is a diagram illustrating the interval ranges employed for detection of tachyarrhythmias in the disclosed embodiment of the present invention.

FIG. 1 illustrates the relationship between the interval ranges associated with detection of fibrillation and tachycardia, as employed in the context of the present invention. The maximum interval indicative of fibrillation (minimum interval indicative of tachycardia), "$FDI_p$" is defined during programming of the device. The maximum interval indicative of tachycardia, TDI, is similarly defined during programming of the device. As illustrated, an increments to ($FDI_p$ plus delta) or decrements from ($FDI_p$ minus delta) the value the value of $FDI_p$ may occur as part of the detection process including the present invention. Initially, $FDI_p$ serves as the current maximum interval indicative of fibrillation ($FDI_c$). As increments or decrements are made, the incremented or decremented values are used as $FDI_c$. Increments are only allowable up to the point where the incremented value would exceed a maximum value ($FDI_{max}$). Decrements are only allowable up to the point where the decremented value would be less than a minimum value ($FDI_{min}$).

In the context of the preferred embodiment of the present invention, four or eight preceding R—R intervals less than TDI, for example, may be examined to determine whether the duration of $FDI_c$ needs to be incremented or decremented. The value of the increment delta may be, for example, 10 to 30 ms, and the values of $FDI_{max}$ and $FDI_{min}$ may be, for example, $FDI_c$ plus 20 to 60 milliseconds and $FDI_c$ minus 20 to 60 milliseconds, respectively. Alternatively, the invention may be practiced in a fashion such that $FDI_p$ defines either the maximum value or the minimum value of $FDI_c$. For example, the physician may wish to allow the device only to become more biased toward detection of ventricular fibrillation, as compared to detection using the programmed rate interval ranges. In this case, $FDI_{min}$ would be set equal to $FDI_p$.

$FDI_c$ may be incremented, for example, in response to more than fifty percent or more of the N intervals being less than $FDI_c$ and $FDI_c$ may correspondingly be decremented in response to more than fifty percent of the N intervals being greater than or equal to $FDI_c$. Alternatively, more stringent criteria for incrementing and decrementing $FDI_c$ may be applied, with incrementing occurring only in response to seventy-five percent or more of the N intervals being less than $FDI_c$ and decrementing occurring only in response to seventy-five percent or more of the N intervals being greater than or equal to $FDI_c$. It is anticipated that in greater than or equal to $FDI_c$. It is anticipated that in commercial embodiments of the present invention, some or all of the values and parameters discussed above will be selectable by the physician.

Figure 2:
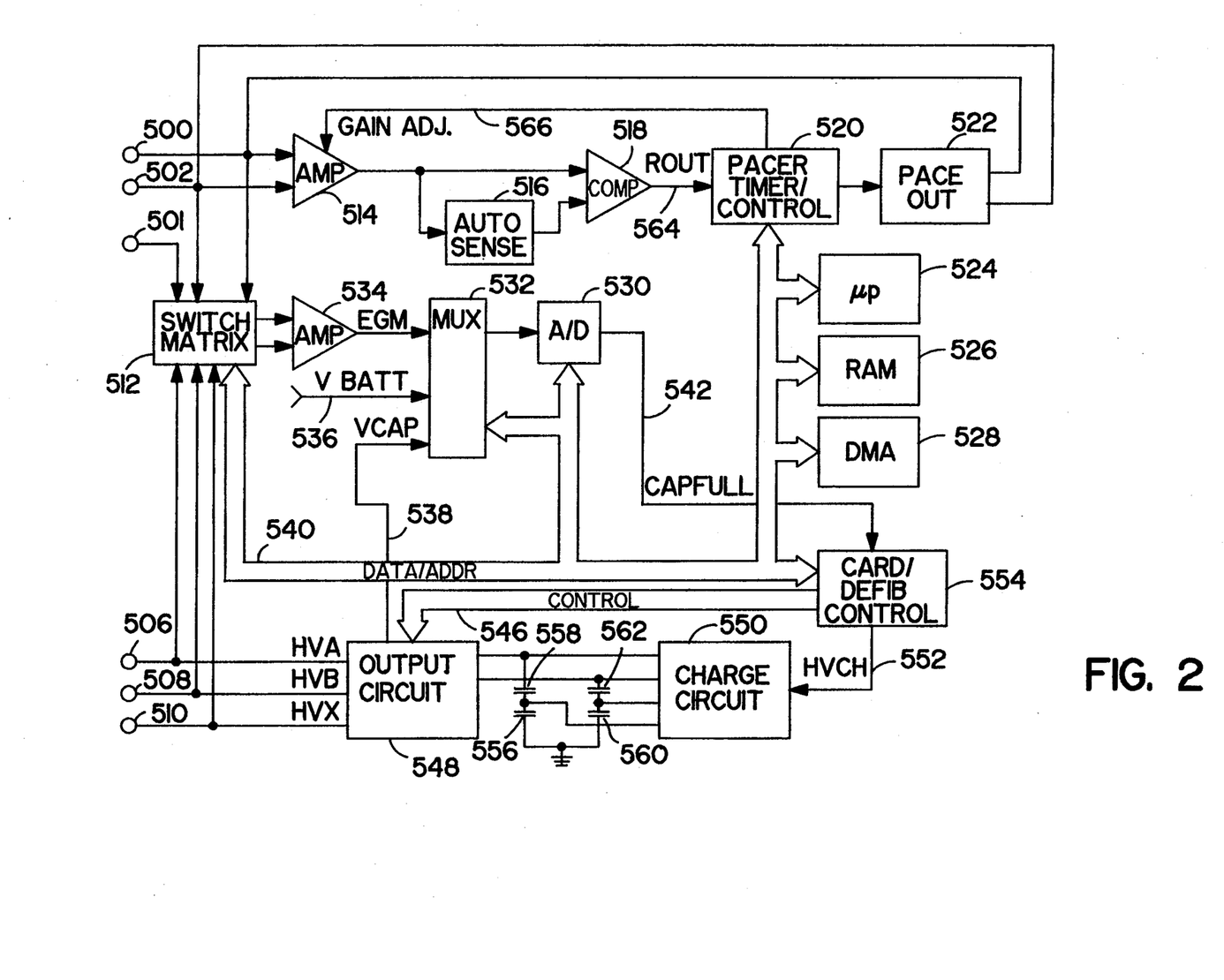
FIG. 2 is a simplified block diagram illustrating the components of a device within which the method and apparatus of the present invention may be implemented.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to any of the implantable pacemaker/defibrillator/cardioverters presently being implanted for clinical evaluation in the United States. The invention is also believed practicable in conjunction with implantable pacemaker/cardioverters/defibrillators as disclosed in prior U.S. Pat. No. 4,548,209, issued to Wielders, et al. on Oct. 22, 1985, U.S. Pat. No. 4,693,253, issued to Adams et al. on Sep. 15, 1987, U.S. Pat. No. 4,830,006, issued to Haluska et al. on May 6, 1989 and U.S. Pat. No. 4,949,719, issued to Pless et al. on Aug. 21, 1990, all of which are incorporated herein by reference in their entireties.

The device is illustrated as being provided with six electrodes, 500, 502, 504, 506, 508 and 510. Electrodes 500 and 502 may be a pair of endocardial electrodes located in the ventricle, mounted to a transvenous lead. Electrode 504 may correspond to a remote, indifferent electrode located on the housing of the implantable pacemaker/cardioverter/defibrillator. Electrodes 506, 508 and 510 may correspond to the large surface area defibrillation electrodes located on ventricular, coronary sinus, superior vena cava or subcutaneous leads or to epicardial defibrillation electrodes.

Electrodes 500 and 502 are shown as hard-wired to the 514, auto threshold circuit 516 for providing an adjustable sensing threshold as a function of the measured R-wave amplitude and comparator 518. A signal is generated on R-out line 564 whenever the signal sensed between electrodes 500 and 502 exceeds the present sensing threshold defined by auto threshold circuit 516. As illustrated, the gain on the band pass amplifier 514 is also adjustable by means of a signal from the pacer timing and control circuitry 520 on GAIN ADJ line 566.

The operation of this R-wave detection circuitry may correspond to that disclosed in commonly assigned, co-pending U.S. patent application Ser. No. 07/612,760, by Keimel, et al., filed November 15, for an Apparatus for Monitoring Electrical Physiologic Signals, incorporated herein by reference in its entirety. However, alternative R-wave detection circuitry such as that illustrated in U.S. Pat. No. 4,819,643, issued to Menken on Apr. 11, 1989 and U.S. Pat. No. 4,880,004, issued to Baker et al. on Nov. 14, 1989, both incorporated herein by reference in their entireties, may also usefully be employed to practice the present invention.

The threshold adjustment circuit 516 sets a threshold corresponding to a predetermined percentage of the amplitude of a sensed R-wave, which threshold decays to a minimum threshold level over a period of less than three seconds thereafter, similar to the automatic sensing threshold circuitry illustrated in the article "Reliable R-Wave Detection from Ambulatory Subjects", by Thakor et al., published in Biomedical Science Instrumentation, Vol. 4, pp 67–72, 1978, incorporated herein by reference in its entirety.

It is preferable that the threshold level not be adjusted in response to paced R-waves, but instead should continue to approach the minimum threshold level following paced R-waves to enhance sensing of low level spontaneous R-paced R-waves to enhance sensing of low level spontaneous R-waves associated with tachyarrhythmias. The time constant of the threshold circuit is also preferably sufficiently short so that minimum sensing threshold may be reached within 1–3 seconds following adjustment of the sensing threshold equal to 70–80% of the amplitude of a detected spontaneous R-wave. The invention may also be practiced in conjunction with more traditional R-wave sensors of the type comprising a band pass amplifier and a comparator circuit to determine when the band-passed signal exceeds a predetermined, fixed sensing threshold.

Switch matrix 512 is used to select which of the available electrodes are coupled to band pass amplifier 534. Selection of which two electrodes are so coupled is controlled by the microprocessor 524 via data/address bus 540. Signals from the selected electrodes are passed through band-pass amplifier 534 and into multiplexer 532, where they are converted to multi-bit digital signals by A/D converter 530, for storage in random access memory 526 under control of direct memory address circuit 528.

Microprocessor 524 analyzes the digitized EGM signal stored in random access memory 526 to determine the width of the stored R-wave or in conjunction with the tachycardia/fibrillation discrimination function discussed below.

Amplifier 534 may be a broad band pass amplifier, having a band pass extending for approximately 0.5 to 200 hertz. The filtered EGM signal from amplifier 534 is passed through multiplexer 532, and digitized in A-D converter circuitry 530. The digitized EGM data is stored in random access memory 526 under control of direct memory address circuitry 528. Preferably, a portion of random access memory 526 is configured as a looping or buffer memory which stores at least the preceding several seconds of the EGM signal.

The data stored in the buffer memory may be optionally employed to perform R-wave width measurements as disclosed in co-pending U.S. patent application Ser. No. 07/867,931, filed Apr. 13, 1992 by Mader et al., incorporated herein by reference in its entirety and/or to perform the ventricular fibrillation/ventricular tachycardia discrimination function disclosed in pending U.S. patent application Ser. No. 07/750,679 filed Aug. 27, 1991 by Bardy et al., also incorporated herein by reference in its entirety. However, the present invention is readily practiced in devices which do not include such functions, and for purposes of the disclosed preferred embodiment of the present invention it should be assumed that such functions, if available, are programmed off.

The microprocessor also updates counts related to the R—R intervals previously sensed. The counts are incremented on the occurrence of a measured R—R intervals falling within associated rate ranges. As discussed above these ranges may include the ranges illustrated above in FIG. 1 associated with ventricular tachycardia and ventricular fibrillation, and the stored counts may include VTEC and VFEC. These rate ranges may be defined by the programming stored in the RAM 526.

These counts, along with other stored information reflective of the previous series of R—R intervals such as information regarding the rapidity of onset of the detected short R—R intervals, the stability of the detected R—R intervals, the duration of continued detection of short R—R intervals, the average R—R interval duration and information derived from analysis of stored EGM segments are used to determine whether tachyarrhythmias are present and to distinguish between different types of tachyarrhythmias, as discussed above in conjunction with FIG. 1. Other such detection algorithms for recognizing tachycardias are described in the above cited U.S. Pat. No. 4,726,380, issued to Vollmann, U.S. Pat. No. 4,880,005, issued to Pless et al. and U.S. Pat. No. 4,830,006, issued to Haluska et al., incorporated by reference in their entireties herein. An additional set of tachycardia recognition methodologies is disclosed in the article "On-set and Stability for Ventricular Tachyarrhythmia Detection in an Implantable pacer-Cardioverter-Defibrillator" by Olson et al., published in *Computers in Cardiology*, Oct. 7–10, 1986, IEEE Computer Society Press, pp. 167–170, also incorporated by reference in its entirety herein. However, other criteria may also be measured and employed in conjunction with the present invention.

It is envisioned that onset and stability requirements are optional in a device employing the present invention, and preferably are made available as programmable options, which may be deleted by external programmer command. If included, it is believed preferable that the onset criteria be required to met prior to initiating counting of VTEC, and that once met, the criteria will remain satisfied until detection of tachycardia termination. Thus, onset is not intended to be a detection criteria required for re-detection of tachycardia, following initial detection. The width criterion, if used, should also be understood to be used both in initial detection of tachycardia and in re-detection of tachycardia. This reflects a presumption that following initial detection of ventricular tachycardia, absent a proven return to normal heart rhythm (termination detect), subsequent high ventricular rates should be presumed to be ventricular in origin. The stability criterion, on the other hand, is believed to be appropriate for use both in initial detection of tachycardia and in re-detection of tachycardia.

The remainder of the circuitry is dedicated to the provision of cardiac pacing, cardioversion and defibrillation therapies. The pacer timing/control circuitry 520 includes programmable digital counters which control the basic time intervals associated with VVI mode cardiac pacing, including the pacing escape intervals, the refractory periods during which sensed R-waves are ineffective to restart timing of the escape intervals and the pulse width of the pacing pulses. The durations of these intervals are determined by microprocessor 524, and are communicated to the pacing circuitry 520 via address/data bus 540. Pacer timing/control circuitry also determines the amplitude of the cardiac pacing pulses and the gain of band-pass amplifier, under control of microprocessor 524.

During VVI mode pacing, the escape interval counter within pacer timing/control circuitry 520 is reset upon sensing of an R-wave as indicated by a signal on line 564, and on timeout triggers generation of a pacing pulse by pacer output circuitry 522, which is coupled to electrodes 500 and 502. The escape interval counter is also reset on generation of a pacing pulse, and thereby controls the basic timing of cardiac pacing functions, including anti-tachycardia pacing. The duration of the interval defined by the escape interval timer is determined by microprocessor 524, via data/address bus 540. The value of the count present in the escape interval counter when reset by sensed R-waves may be used to measure the duration of R—R intervals, to detect the presence of tachycardia and to determine whether the minimum rate criteria are met for activation of the width measurement function.

Microprocessor 524 operates as an interrupt driven device, and responds to interrupts from pacer timing-/control circuitry 520 corresponding to the occurrence of sensed R-waves and corresponding to the generation of cardiac pacing pulses. These interrupts are provided via data/address bus 540. Any necessary mathematical calculations to be performed by microprocessor 524 and any updating of the values or intervals controlled by pacer timing/control circuitry 520 take place following such interrupts.

In the event that a tachyarrhythmia is detected, and an anti-tachyarrhythmia pacing regimen is desired, appropriate timing intervals for controlling generation of anti-tachycardia pacing therapies are loaded from microprocessor 524 into the pacer timing and control circuitry 520, to control the operation of the escape interval counter and to define refractory periods during which detection of an R-wave by the R-wave detection circuitry is ineffective to restart the escape interval counter. Similarly, in the event that generation of a cardioversion or defibrillation pulse is required, microprocessor 524 employs the counters to in timing and control circuitry 520 to control timing of such cardioversion and defibrillation pulses, as well as timing of associated refractory periods during which sensed R-waves are ineffective to reset the timing circuitry.

In response to the detection of fibrillation or a tachycardia requiring a cardioversion pulse, microprocessor 524 activates cardioversion/defibrillation control circuitry 554, which initiates charging of the high voltage capacitors 556, 558, 560 and 562 via charging circuit 550, under control of high voltage charging line 552. The voltage on the high voltage capacitors is monitored via VCAP line 538, which is passed through multiplexer 532, and, in response to reaching a predetermined value set by microprocessor 524, results in generation of a logic signal on CAP FULL line 542, terminating charging. Thereafter, delivery of the timing of the defibrillation or cardioversion pulse is controlled by pacer timing/control circuitry 520. One embodiment of an appropriate system for delivery and synchronization of cardioversion and defibrillation pulses, and controlling the timing functions related to them is disclosed in more detail in co-pending, commonly assigned U.S. patent application Ser. No. 07/612,761, by Keimel, for an Apparatus for Detecting and Treating a Tachyarrhythmia, filed Nov. 15, 1990 and incorporated herein by reference in its entirety. However, any known cardioversion or defibrillation pulse generation circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al., cited above, and in U.S. Pat. No. 4,375,817, issued to Engle et al., all incorporated herein by reference in their entireties may also be employed. Similarly, known circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties may also be used.

In modern pacemaker/cardioverter/defibrillators, the particular anti-tachycardia and defibrillation therapies are programmed into the device ahead of time by the physician, and a menu of therapies is typically provided. For example, on initial detection of tachycardia, an anti-tachycardia pacing therapy may be selected. On re-detection of tachycardia, a more aggressive anti-tachycardia pacing therapy may be scheduled. If repeated attempts at anti-tachycardia pacing therapies fail, a higher level cardioversion pulse therapy may be selected thereafter. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al. The present invention is believed practicable in conjunction with any of the known anti-tachycardia pacing and cardioversion therapies, and it is believed most likely that the invention of the present application will be practiced in conjunction with a device in which the choice and order of delivered therapies is programmable by the physician, as in current implantable pacemaker/cardioverter/defibrillators.

In addition to varying the therapy delivered following a failed attempt to terminate a tachyarrhythmia, it is also known that adjustment of detection criteria may be appropriate. For example, adjustment may comprise reducing the number of intervals required to detect a tachyarrhythmia to allow a more rapid re-detection or by changing the interval ranges to bias detection towards detection of ventricular fibrillation, for example as disclosed in U.S. Pat. No. 4,971,058, issued to Pless et al. and incorporated herein by reference in its entirety.

In the present invention, selection of the particular electrode configuration for delivery of the cardioversion or defibrillation pulses is controlled via output circuit 548, under control of cardioversion/defibrillation control circuitry 554 via control bus 546. Output circuit 548 determines which of the high voltage electrodes 506, 508 and 510 will be employed in delivering the defibrillation or cardioversion pulse regimen, and may also be used to specify a multi-electrode, simultaneous pulse regimen or a multi-electrode sequential pulse regimen. Monophasic or biphasic pulses may be generated. One example of circuitry which may be used to perform this function is set forth in commonly assigned co-pending patent application Ser. No. 07/612,758, filed by Keimel, for an Apparatus for Delivering Single and Multiple Cardioversion and Defibrillation Pulses, filed Nov. 14, 1990, incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in the context of the present invention. Alternatively single monophasic pulse regimens employing only a single electrode pair according to any of the above cited references which disclose implantable cardioverters or defibrillators may also be used.

Figure 3A:
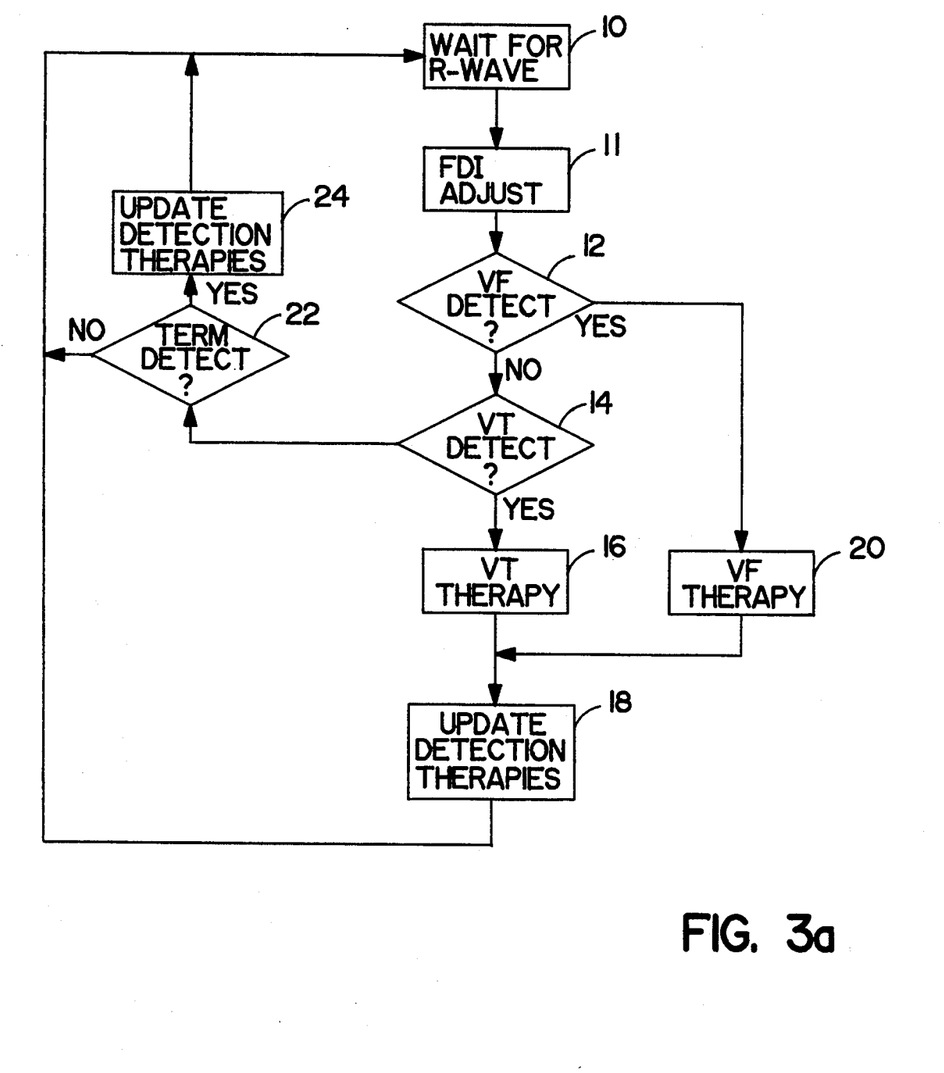
FIG. 3 is a simplified flow chart diagram illustrating the functioning of the present invention.
Figure 3B:
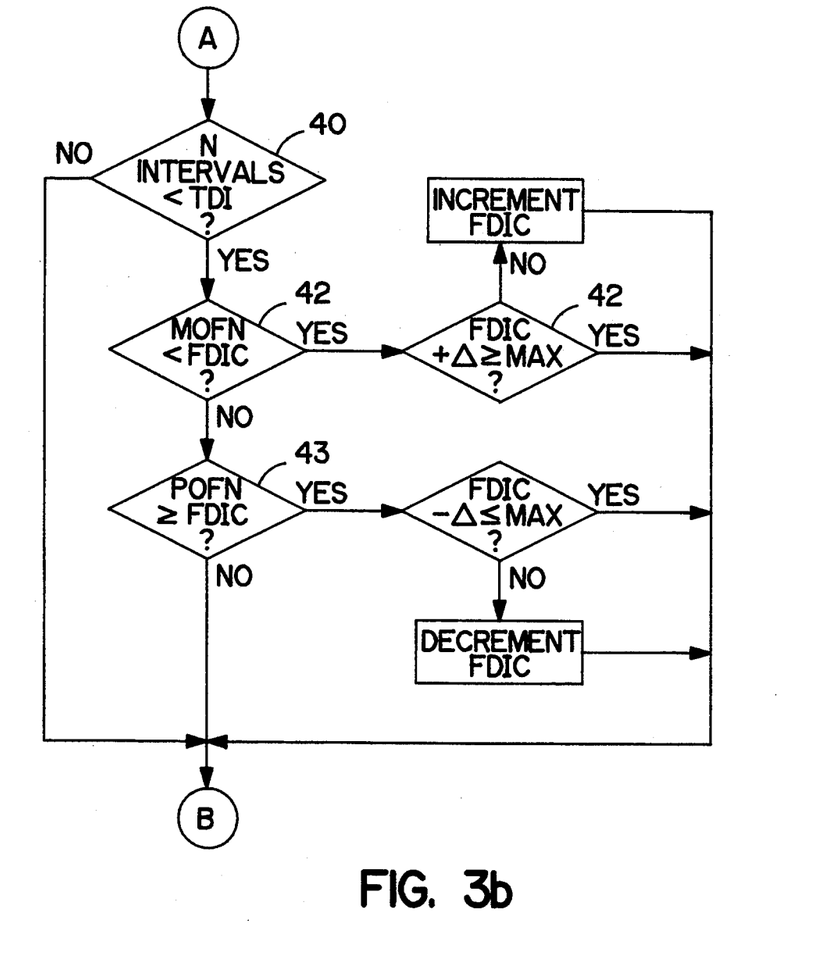

FIGS. 3a and 3b illustrate the function of the present invention as embodied in a device as illustrated in FIG. 2, in the form of flow charts. FIG. 3b illustrates the FDI ADJUST functional block 11 of FIG. 3a in more detail.

FIG. 3a illustrates the overall tachyarrhythmia detection function as employed in the disclosed embodiment of the present invention. With the exception of functional block 11, this portion of the tachyarrhythmia detection function corresponds to that employed in the Medtronic Model 7216 and 7217 implantable pacemaker/cardioverter/defibrillators, discussed above. In the context of FIG. 3a, the device should be understood to be operating as a demand pacer, with the detection functions illustrated taking place during the refractory period following the occurrence of a spontaneous or paced R-wave.

The microprocessor waits at 10 for an interrupt indicating the occurrence of a paced or sensed R-wave and in response thereto stores the duration of the preceding R—R interval and increments the value of VFEC or VTEC, if appropriate, using the interval criteria discussed above, based on the value of $FDI_c$ and TDI. The microprocessor then determines whether the value of $FDI_c$ needs to be incremented or decremented at 11. At 12, the microprocessor determines whether the detection criteria for ventricular fibrillation have been met, i.e., whether VFEC is greater than or equal to VFNID. If ventricular fibrillation is detected, then the scheduled defibrillation therapy is initiated in block 16 and the detection criteria and therapy menus are updated at 18, as described above.

If ventricular fibrillation is not detected at 12, the microprocessor checks at 14 to determine whether the criteria for detection of ventricular tachycardia have been met, i.e. whether VTEC is greater than or equal to VTNID. If ventricular tachycardia is detected, the scheduled ventricular tachycardia therapy is delivered at 16 and the detection criteria and therapy menus are updated at 18, as described above.

If no tachyarrhythmia is detected, if a tachycardia was previously detected, the microprocessor checks at 22 to determine whether a return to sinus rhythm has occurred, i.e. a series of a predetermined number of R—R intervals greater than or equal to TDI. If termination is detected, the detection criteria and therapy menus are updated at 24, as described above.

The flow chart of FIG. 3b illustrates the method by which the value of $FDI_c$ is adjusted in block 11 of FIG. 3a, based on the proportion of the N most recent event intervals that are shorter than the $FDI_c$ value. Decision block 40 determines whether or not N event intervals less than TDI have been stored since the last updating of the detection criteria due to detection of a tachyarrhythmia or detection of termination of a tachyarrhythmia. If not, the adjustment function is not enabled, and the microprocessor continues with the detection methodology of FIG. 3a. N is intended to be a relatively small number, e.g. four or eight, preferably less than VFNID or VTNID, so detection of fibrillation or tachycardia, as a practical matter will not occur until there has at least been an opportunity for the adjustment function to operate.

If N intervals less than TDI have been detected, decision block 42 determines whether or not a predetermined number of the N intervals are less than the value of $FDI_c$. If a predetermined number M of the of the N stored event intervals are less than $FDI_c$, for example three or more of four, the microprocessor will check at 44 to determine whether $FDI_c$ is already at its maximum value. If it is at its maximum value, then it is not altered, and the present value of $FDI_c$ is employed in the detection methodology of FIG. 3a. However, if $FDI_c$ is not yet at its programmed maximum value, then $FDI_c$ is incremented by delta in block 46.

If M of the of the N stored event intervals are not less than $FDI_c$, the microprocessor will check at 43 to determine whether P of the of the N stored intervals are greater than or equal to $FDI_c$, for example three or more of four.

If not, the adjustment function is not enabled, and the microprocessor continues with the detection methodology of FIG. 3a. If P of the N intervals are greater than or equal to $FDI_c$, the microprocessor checks at 48 to determine whether $FDI_c$ is already at its minimum value. If it is at its minimum value, then it is not altered, and the present value of $FDI_c$ is employed in the detection methodology of FIG. 3a. However, if $FDI_c$ is not yet at its programmed minimum value, then $FDI_c$ is decremented by delta in block 50.

Through these adjustments of the $FDI_c$, the detection function illustrated in Figure #a is rendered more sensitive to the trend of the N most recent event intervals. It is thus expected, that in practice the adjustment of the $FDI_c$ will prove beneficial in accelerating a detection of ventricular tachycardia or ventricular fibrillation in those cases in which the R—R intervals of the patient's tachyarrhythmia include intervals greater and less than FDI.

After incrementing or decrementing the value of $FDI_c$, the new value is used in subsequent detection functions illustrated in FIG. 3a. The new value of $FDI_c$ may be employed in various ways. The simplest manner in which the new value of $FDI_c$ may be employed is for subsequent R—R intervals to be classified based on the new value, with the classification of preceding R—R intervals left undisturbed. In this case, the vales of VFEC and VTEC would remain unaltered as a result of the adjustment function, and would simply be subsequently incremented using the new interval ranges defined using the adjusted value of $FDI_c$.

An alternative method of employing the adjusted value of $FDI_c$ is to apply the new interval ranges defined by the adjusted value both prospectively and retrospectively. In this case, previously stored R—R intervals would be reexamined, and the VFEC and VTEC counts updated to the values which they would have had if the adjusted value of $FDI_c$ had been in effect throughout the detection sequence.

Following a completed detection sequence or detection of termination of a previously detected tachyarrhythmia, the value of $FDI_c$ is reset to be equal to $FDI_p$, as part of the procedure for updating the detection criteria in functional blocks 18 and 24 in FIG. 3a. In some embodiments of the invention, the value of $FDI_p$ may be different during re-detection sequences from the value during initial detection sequences. In such cases, during re-detection sequences, the adjustment function may be employed using $FDI_c$ set to the current value of $FDI_p$. Alternatively, in such embodiments and in other embodiments of the invention, the adjustment function may be dispensed with entirely during re-detection sequences.

While the preferred embodiment of the device takes the form of a microprocessor controlled device as illustrated in FIG. 2, in which the various functional steps illustrated in FIGS. 3a and 3b would be implemented in the form of software, the invention may equally well be practiced in the form of a dedicated, full custom digital integrated circuit or, even in the form of an analog circuit, employing analog values as substitutes for the digital values disclosed in conjunction with the above specification.

In addition, while the preferred embodiment disclosed above takes the form of a pacemaker/cardioverter/defibrillator, the enhanced ability to distinguish between various tachyarrhythmias and the improved speed of detection provided by the present invention are also valuable and applicable to devices which are only capable of performing a subset of the various therapies discussed above in conjunction with FIG. 2. For example, the ability to accurately distinguish between ventricular tachycardia and ventricular fibrillation would be valuable in an anti-tachycardia pacemaker, even without a cardioversion pulse generator, to determine whether anti-tachycardia pacing therapies are appropriate. Similarly, the ability to distinguish between ventricular tachycardia and ventricular fibrillation is valuable in an implantable cardioverter/defibrillator lacking a cardiac pacing function, for example, as in the currently available CPI AICD implantable cardioverter/defibrillators. It should further be kept in mind that while the therapies described for delivery in response to detection of the various arrhythmias discussed are all disclosed in the context of electrical therapies, it is possible that the invention may be embodied in the form of an implantable drug dispenser, wherein one or more of the anti-tachycardia therapies takes the form of injection of a drug locally into the heart or systemically to treat the detected arrhythmia. As such, the above disclosure should be taken merely as an example of an embodiment of the present invention, rather than limiting, when reading the claims which follow.

In conjunction with the above specification, I claim:

I claim:

1. An apparatus for detection and treatment of tachyarrhythmias, comprising:
   means for sensing depolarizations of a patient's heart;
   means for measuring the intervals separating successive depolarizations of said patient's heart;
   means for defining a first interval range extending between a first interval duration and a second interval duration less than said first interval duration and a second interval range extending between said second interval duration and a third interval duration less than said second interval duration;
   means for determining the number of said measured intervals falling within said first interval range and for determining the number of said measured intervals falling within said second interval range;
   first diagnosing means for diagnosing the occurrence of a first type of arrhythmia when the number of said measured intervals falling within said first interval range equals a first predetermined number;
   second diagnosing means for diagnosing the occurrence of a second type of arrhythmia when the number of measured intervals falling within said second interval range equals a second predetermined number;
   interval range adjustment means responsive to said determining means for adjusting said second interval duration, for subsequent use by said determining means, as a function of the durations of a preceding series of a third predetermined number of said measured intervals, said third number less than either said first or second number;
   means for delivering a first anti-arrhythmia therapy in response to detection of said first type of arrhythmia;
   means for delivering a second anti-arrhythmia therapy in response to detection of said second type of arrhythmia.

2. An apparatus according to claim 1 wherein said adjustment means comprises means for determining the relative numbers of said measured intervals falling within said first and second interval ranges within said preceding series.

3. An apparatus according to claim 2 wherein said adjusting means comprises means for increasing said second interval duration in response to the number of said measured intervals within said preceding series and falling within said second interval range equalling or exceeding a predetermined first value.

4. An apparatus according to claim 2 wherein said adjusting means comprises means for decreasing said second interval duration in response to the number of said measured intervals within said preceding series and falling within said first interval range equalling or exceeding a predetermined second value.

5. An apparatus according to claim 1 or claim 2 wherein said first diagnosing means comprises means for diagnosing the occurrence of a tachycardia and wherein said second diagnosing means comprises means for diagnosing the occurrence of fibrillation.

6. An apparatus according to claim 1 or claim 2 wherein said means for sensing depolarizations comprises means for sensing depolarizations of said patient's ventricle.

7. An apparatus according to claim 1 or claim 2 wherein said first and second predetermined values comprise predetermined numbers of said measured intervals falling within said first and second interval ranges, respectively.

8. An apparatus according to claim 1 or claim 2 wherein said means for determining the number of said measured intervals falling within said second interval range comprises means for determining the number of said measured intervals within a preceding series of a fourth predetermined number of said measured intervals falling within said second interval range.

9. An apparatus according to claim 1 or claim 2 wherein said means for determining the number of said measured intervals falling within said first interval range comprises means for counting the number of said measured intervals falling within said first interval range, and for resetting the count of said measured intervals falling within said first interval range in response to the occurrence of a said measured interval falling outside said first and second interval ranges.

10. An apparatus for detecting and treating tachycardia and fibrillation, comprising:
- means for sensing depolarizations of a patient's heart;
- means for measuring the intervals between successive depolarizations of said patient's heart;
- means for defining a first range of intervals indicative of the occurrence of a tachycardia, including intervals falling between a first predetermined duration (TDI) and a second predetermined duration (FDI), wherein FDI is less than TDI;
- means for defining a second interval range indicative of fibrillation, said second range including intervals less than FDI;
- means for determining the numbers of said measured intervals falling within said first and second interval ranges;
- first means for diagnosing the occurrence of tachycardia when the number of said measured intervals falling within said first interval range equals a first predetermined number;
- second means for diagnosing the occurrence of fibrillation when the number of said measured intervals falling within said second interval range equals a second predetermined number;
- interval range adjustment means responsive to said determining means for adjusting FDI for subsequent use by said first and second diagnosing means as a function of the durations of a preceding series of a third predetermined number of said measured intervals, said third number less than either said first or second number;
- means for delivering an anti-tachycardia therapy in response to a diagnosis of tachycardia by said first diagnosing means;
- means for delivering a defibrillation therapy in response to a diagnosis of fibrillation by said second diagnosing means.

* * * * *